United States Patent

Bonutti

[11] Patent Number: 5,845,645
[45] Date of Patent: Dec. 8, 1998

[54] METHOD OF ANCHORING A SUTURE

[76] Inventor: Peter M. Bonutti, 1303 W. Evergreen Plz., Effingham, Ill. 62401

[21] Appl. No.: 829,095

[22] Filed: Mar. 31, 1997

Related U.S. Application Data

[60] Continuation-in-part of Ser. No. 667,549, Jun. 21, 1996, Pat. No. 5,733,306, which is a division of Ser. No. 452,310, May 26, 1995, Pat. No. 5,584,862, which is a continuation-in-part of Ser. No. 62,295, May 14, 1993, Pat. No. 5,403,348.

[51] Int. Cl.[6] .................................................. A61B 19/00
[52] U.S. Cl. .......................................... 128/898; 606/232
[58] Field of Search ..................................... 606/232, 139, 606/72–76, 144, 220, 151; 128/898

[56] References Cited

U.S. PATENT DOCUMENTS

| | | |
|---|---|---|
| 4,235,238 | 11/1980 | Oglu et al. . |
| 4,409,974 | 10/1983 | Freeland .............................. 606/232 X |
| 4,669,473 | 6/1987 | Richards et al. ..................... 606/232 X |
| 4,741,330 | 5/1988 | Hayhurst . |
| 4,750,492 | 6/1988 | Jacobs ................................. 606/232 X |
| 4,823,794 | 4/1989 | Pierce ....................................... 606/232 |
| 4,898,156 | 2/1990 | Gatturna et al. ..................... 606/232 X |
| 4,968,315 | 11/1990 | Gatturna .............................. 606/232 X |
| 5,009,663 | 4/1991 | Broome' ................................. 606/232 |
| 5,037,422 | 8/1991 | Hayhurst et al. .................... 606/232 X |
| 5,041,129 | 8/1991 | Hayhurst et al. . |
| 5,046,513 | 9/1991 | Gatturna et al. ........................ 128/898 |
| 5,100,417 | 3/1992 | Cerier et al. ............................ 606/139 |
| 5,123,941 | 6/1992 | Cope ....................................... 606/232 |
| 5,203,787 | 4/1993 | Noblitt et al. . |
| 5,403,348 | 4/1995 | Bonutti ................................... 606/232 |
| 5,405,359 | 4/1995 | Pierce . |
| 5,464,426 | 11/1995 | Bonutti . |
| 5,527,343 | 6/1996 | Bonutti . |
| 5,534,012 | 7/1996 | Bonutti . |
| 5,549,630 | 8/1996 | Bonutti ................................... 606/232 |
| 5,584,862 | 12/1996 | Bonutti ................................... 606/232 |

*Primary Examiner*—David H. Wilise
*Assistant Examiner*—Kelly O'Hara
*Attorney, Agent, or Firm*—Tarolli, Sundheim, Covell, Tummino & Szabo

[57] ABSTRACT

To anchor a suture, the suture is inserted through passages which are spaced apart along and extend transversely to a longitudinal central axis of an anchor. When the anchor is moved into body tissue, a first portion of the suture extends from the first passage in the anchor through an opening in the body tissue to a location disposed to one side of the body tissue. A second portion of the suture extends from the second passage in the anchor through the opening in the body tissue. The suture is tensioned to apply force to the anchor. The force applied to the anchor by the suture initiates tipping of the anchor and movement of an end surface on the anchor across a leading end surface on an inserter member.

12 Claims, 3 Drawing Sheets

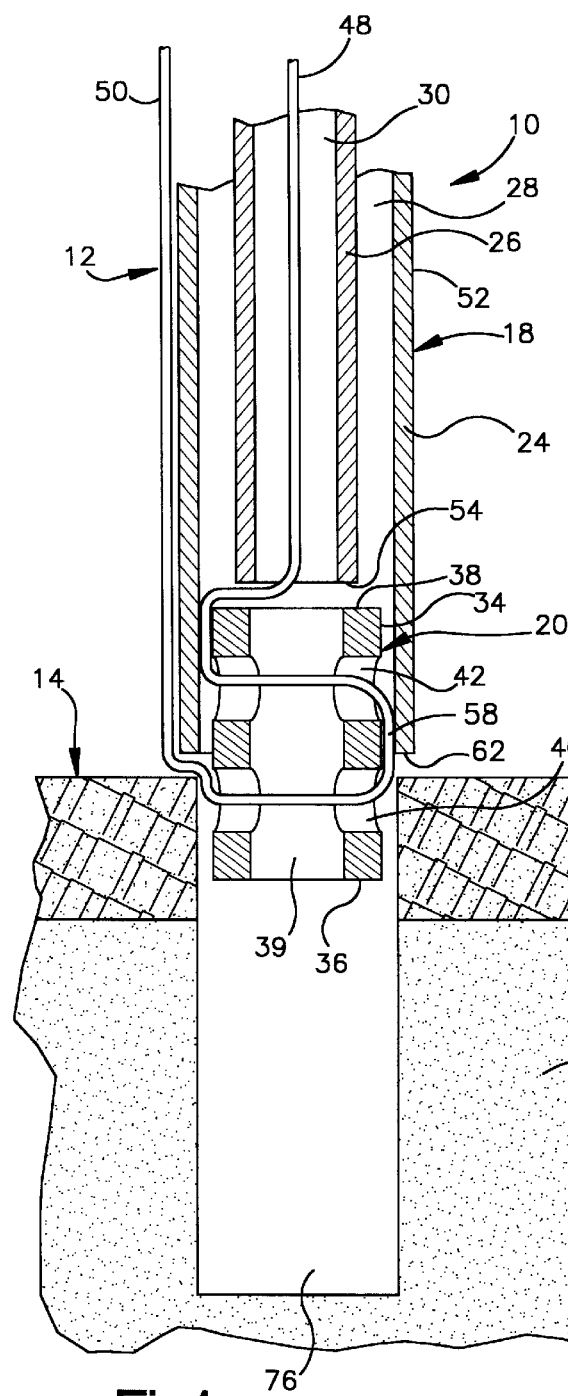
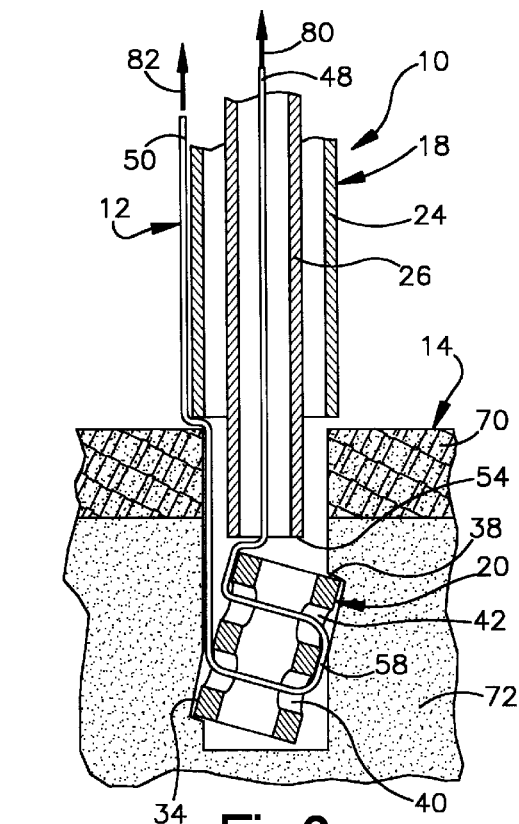
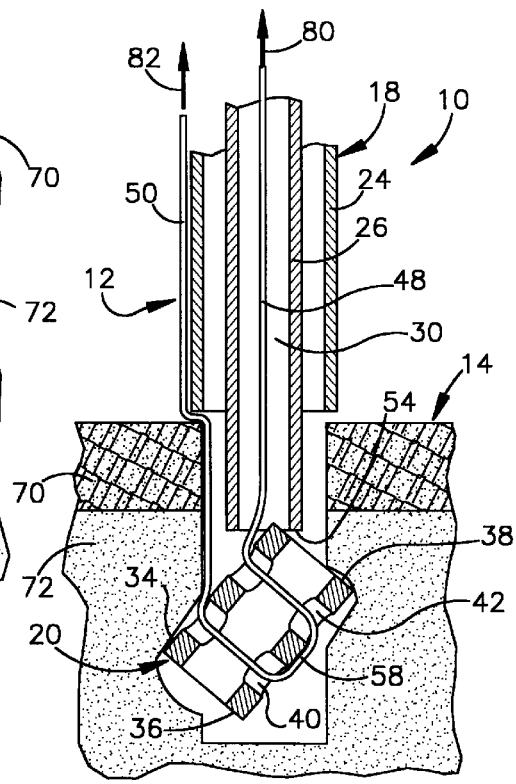

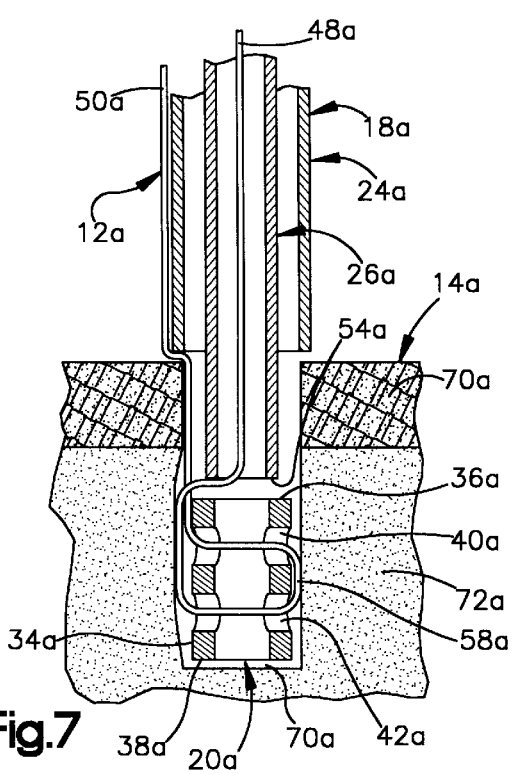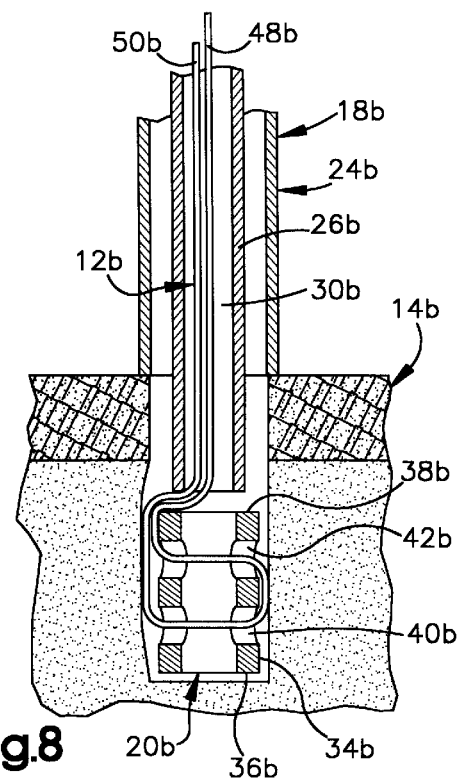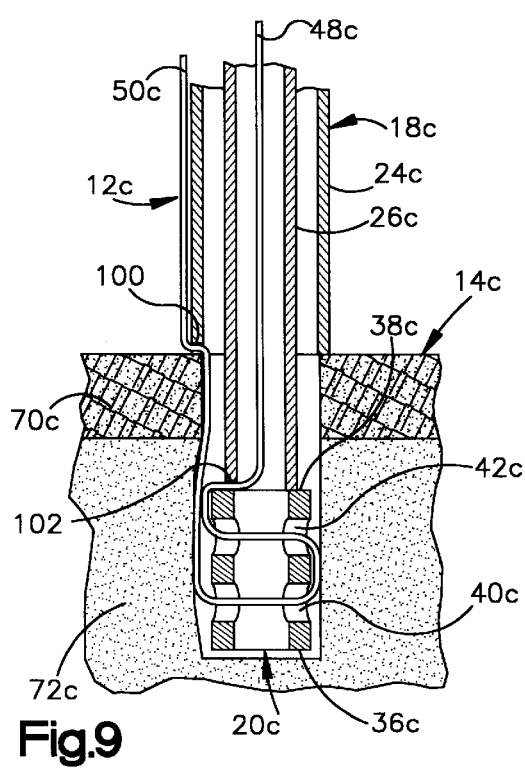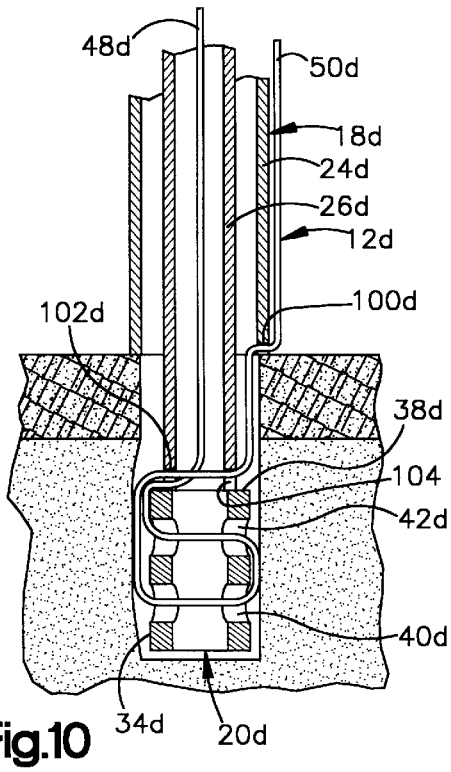

METHOD OF ANCHORING A SUTURE

RELATED APPLICATIONS

This application is a continuation-in-part of U.S. patent application Ser. No. 08/667,549 filed Jun. 21, 1996 now U.S. Pat. No. 5,733,306. The aforementioned application Ser. No. 08/667,549 is itself a divisional of U.S. patent application Ser. No. 08/452,310 filed May 26, 1995 and issued as U.S. Pat. No. 5,584,862. The aforementioned application Ser. No. 08/452,310 is itself a continuation-in-part of U.S. patent application Ser. No. 08/62,295 filed May 14, 1993 and now issued as U.S. Pat. No. 5,403,348. The benefit, under Title 35, United States Code, §120 of the aforementioned applications is hereby claimed.

BACKGROUND OF THE INVENTION

The present invention relates to a new and improved method of anchoring a suture in body tissue.

Known method s of anchoring a suture in body tissue are disclosed in U.S. Pat. Nos. 5,534,012; 5,527,343; and 5,464,426. Although the known methods disclosed in the aforementioned patents provide for the satisfactory anchoring of a suture in body tissue, there is always a need to improve the pull-out force which can be applied against the suture without damaging the suture and/or dislodging the anchor from the body tissue. In addition, there is always a need to improve the manner in which the anchor is oriented relative to the body tissue.

SUMMARY OF THE INVENTION

The present invention provides a new and improved method of anchoring a suture in body tissue. The method includes inserting a suture through a pair of spaced apart transverse passages in an anchor. The suture is moved into body tissue with an end surface on the anchor in engagement with a leading end of an inserter member.

When the anchor has been moved into the body tissue, the suture is tensioned and the anchor is tipped under the influence of force applied to the anchor by the suture. Tipping of the anchor results in movement of the anchor to a position in which the longitudinal central axis of the anchor extends transverse to a longitudinal central axis of the inserter member.

BRIEF DESCRIPTION OF THE DRAWINGS

The foregoing and other features of the invention will become more apparent upon a consideration of the following description taken in connection with the accompanying drawings, wherein:

FIG. 1 is a simplified schematic sectional view illustrating the manner in which a suture anchor is moved into an opening in body tissue;

FIG. 2 is a simplified schematic sectional view, generally similar to FIG. 1, but on a reduced scale, illustrating the manner in which force is applied against the anchor by a suture to initiate tipping of the anchor;

FIG. 3 is a simplified schematic sectional view, generally similar to FIG. 2, illustrating the manner in which an end of the anchor is moved across an end of an inserter member as the anchor is tipped;

FIG. 7 is a simplified sectional view, generally similar to FIG. 1, depicting an alternative orientation of the suture anchor relative to the inserter member during movement of the suture anchor into body tissue;

FIG. 8 is a simplified sectional view, generally similar to FIG. 1, depicting an alternative manner of positioning the suture relative to the inserter member;

FIG. 9 is a simplified sectional view of a second embodiment of the inserter member; and FIG. 10 is a simplified schematic sectional view depicting another manner of positioning the suture relative to the inserter member.

DESCRIPTION OF SPECIFIC PREFERRED EMBODIMENTS OF THE INVENTION

General Description

Figure 4:
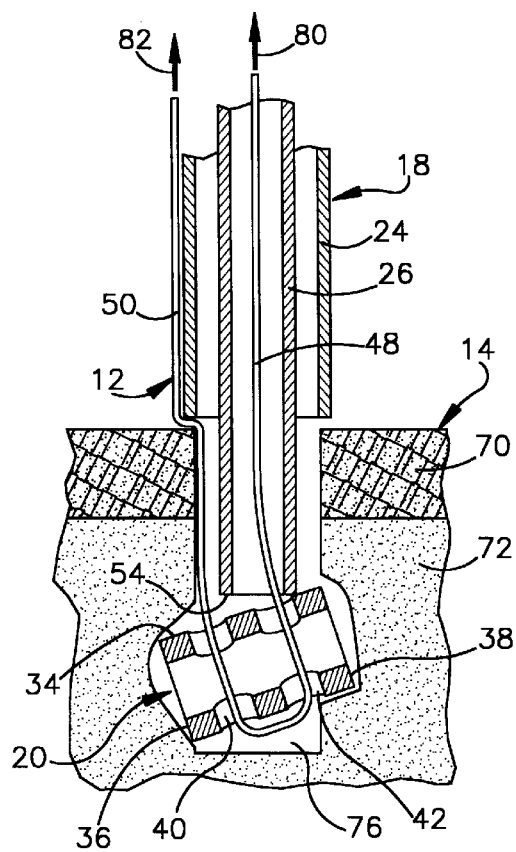
FIG. 4 is a simplified schematic sectional view, generally similar to FIG. 3, further illustrating the manner in which the anchor is tipped.

An apparatus 10 for anchoring a suture 12 in body tissue 14 is illustrated schematically in FIG. 1. The apparatus 10 includes an inserter assembly 18 and an anchor 20. The inserter assembly 18 is used to move the anchor 20 into the body tissue 14.

The inserter assembly 18 includes a tubular cylindrical outer member 24. A tubular cylindrical inner member 26 is disposed in a cylindrical passage 28 in the outer member 24. The inner member 26 is disposed in a coaxial relationship with the outer member 24. The inner member 26 has a cylindrical central passage 30 through which the suture 12 extends.

Although one specific inserter assembly 18 has been shown in FIG. 1, it is contemplated that a different inserter assembly could be utilized if desired. For example, the anchor 20 could be positioned relative to either hard or soft body tissue with an inserter assembly having the construction disclosed in U.S. Pat. application Ser. No. 08/673,923, filed Jul. 1, 1996 now U.S. Pat. No. 5,782,862 by Peter M. Bonutti and entitled ANCHOR INSERTER ASSEMBLY AND METHOD. Alternatively, the inserter assembly could be constructed as disclosed in the now allowed U.S. patent application Ser. No. 08/752,005, filed Nov. 15, 1996 by Peter M. Bonutti and entitled METHOD AND APPARATUS FOR USE IN ANCHORING A SUTURE.

The anchor 20 has a cylindrical outer side surface 34 which extends between an annular leading end surface 36 and an annular trailing end surface 38 on the anchor. An optional cylindrical central passage 49 extends axially through the anchor 20 and has a central axis which is coincident with a longitudinal central axis of the anchor. A pair of cylindrical transverse passages 40 and 42 extend diametrically through the anchor 20. The transverse passages 40 and 42 have parallel central axes which extend perpendicular to and intersect the longitudinal central axis of the anchor 20.

The illustrated anchor 20 is formed of metal, that is, stainless steel. However, it is contemplated that the anchor 20 could be formed of different materials if desired. For example, the anchor 20 could be formed of body tissue, polymeric materials or biodegradable materials. The anchor 20 may be formed in the manner disclosed in U.S. patent application Ser. No. 08/699,553 now U.S. Pat. No. 5,718,717, filed on Aug. 19, 1996 by Peter M. Bonutti and entitled SUTURE ANCHOR. Alternatively, the anchor 20 may be formed in the manner disclosed in U.S. patent application Ser. No. 08/626,393 now U.S. Pat. No. 5,713,921, filed on Mar. 29, 1996 by Peter M. Bonutti and entitled SUTURE ANCHOR.

The illustrated anchor 20 has a length of approximately 0.144 inches and an outside diameter of approximately 0.072 inches. The transverse passages 40 and 42 have central axes which are spaced approximately 0.060 inches apart. Each of the circular transverse passages 40 and 42 has a diameter of approximately 0.035 inches. The central axis of the passage 40 is spaced approximately 0.042 inches from the leading end surface 36 of the anchor 20. Similarly, the central axis of the transverse passage 42 is spaced approximately 0.042 inches from the trailing end surface 38 of the anchor 20.

It should be understood that the foregoing specific materials and dimensions for the anchor 20 have been set forth herein for purposes of clarity of description. It is contemplated that the anchor 20 may be formed of many different materials and have many different dimensions. It should also be understood that the outer side surface 34 of the anchor 20 could have a polygonal configuration rather than the illustrated cylindrical configuration. For example, the anchor 20 could have a configuration similar to the configuration disclosed in U.S. Pat. No. 5,534,012.

The suture 12 has an inner leg or portion 48 which extends along the passage 30 in the inner inserter member 26. The suture 12 has an outer leg 50 which extends generally parallel to the inner leg 48. The outer leg 50 of the suture 12 is disposed along a cylindrical outer side surface 52 of the outer inserter member 24. The inner and outer legs 48 and 50 of the suture 12 extend to a remote location (not shown) which is offset to one side of the body tissue 14.

The inner leg 48 of the suture 12 extends between an annular leading end surface 54 on the inner inserter member 26 and the trailing end surface 38 on the anchor 20. The inner leg 48 of the suture 12 extends through the transverse passage 42 in the anchor to a connector portion 58 of the suture 12. The connector portion 58 of the suture 12 extends between the transverse passages 40 and 42 and the inner and outer legs 48 and 50 of the suture. If desired, the connector portion 58 could be disposed within the anchor 20.

The outer leg 50 of the suture extends across an annular leading end surface 62 of the outer inserter member 24. The outer leg 50 of the suture 12 extends through the transverse passage 40 in the anchor 20 to the connector portion 58 of the suture. The connector portion 58 of the suture engages a portion of the outer side surface 34 on the anchor 20 disposed between the two transverse passages 40 and 42.

Positioning of Anchor

In the embodiment of the invention illustrated in FIGS. 1–6, the anchor 20 is positioned relative to body tissue 14 which is bone in a living human body. The body tissue 14 includes a relatively hard outer layer or cortical bone 70 and a relatively soft inner layer or cancellous bone 72. A cylindrical recess 76 is drilled through the outer layer 70 of cortical bone into the soft inner layer 72 of cancellous bone.

The suture 12 is inserted through the transverse passages 40 and 42 in the anchor 20, in the manner illustrated in FIG. 1. The trailing end surface 38 of the anchor 20 is then positioned adjacent to the leading end surface 54 on the inner inserter member 26. The inner leg 48 of the suture 12 extends through the passage 30 in the inner inserter member 26. A portion of the inner leg 48 of the suture 12 extends across a portion of the trailing end surface 38 of the anchor 20 and across the leading end surface 54 on the inner inserter member 26.

The outer leg 50 of the suture extends from the transverse passage 40 along the outside of the outer inserter member 24. At this time, the anchor 20 is partially enclosed by the outer inserter member 24 and extends axially outward of the leading end surface 62 of the outer inserter member. The anchor 20 is held against movement relative to the inserter members 24 and 26 by tension in the suture 12. The outer inserter member 24 holds the anchor 20 against sidewise tipping movement relative to the inner inserter member 26.

The exposed leading portion of the anchor 20 is then moved through a circular opening to the body tissue recess 76, in the manner illustrated schematically in FIG. 1. The tension in the inner and outer legs 48 and 50 of the suture 12 is then relaxed. The inner inserter member 26 is then moved axially downward (as viewed in FIG. 1) relative to the outer inserter member 24 to push the anchor 20 into the body tissue recess 76.

As this occurs, force is applied by the leading end surface 54 of the inner inserter member 26 against the portion of the inner leg 48 of the suture disposed between the anchor 20 and the inner inserter member. In addition, force is applied by the leading end surface 54 of the inner inserter member 26 against the trailing end surface 38 on the anchor 20. This force pushes the anchor 20 into the recess 76.

Figure 5:
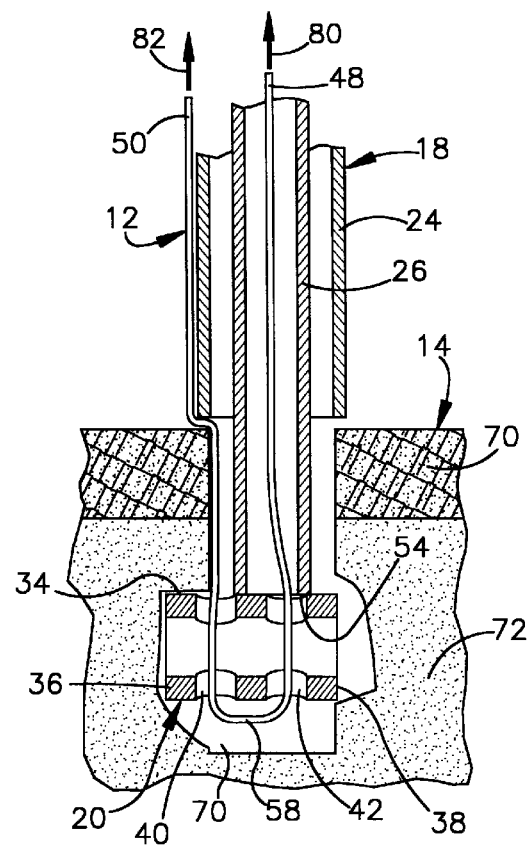
FIG. 5 is a simplified schematic sectional view illustrating the manner in which the anchor is pressed against the inserter member.

After the anchor 20 has been moved into the recess 76, the orientation of the anchor is changed from the initial orientation illustrated in FIG. 1 through the orientations shown in FIGS. 2, 3 and 4 to the retaining orientation shown in FIG. 5. When the anchor 20 is in the initial orientation (FIG. 1), a longitudinal central axis of the anchor extends parallel to longitudinal central axes of the outer and inner inserter members 24 and 26. When the anchor 20 is in the retaining orientation shown in FIG. 5, the longitudinal central axis of the anchor 20 extends perpendicular to and intersects the coincident longitudinal central axes of the outer and inner inserter members 24 and 26.

To initiate movement of the anchor from the initial orientation shown in FIG. 1 toward the retaining orientation shown in FIG. 5, the inner leg 48 of the suture 12 is tensioned. This results in the application of force by the inner leg 48 of the suture 12 against the outer side surface 34 of the anchor 20. The inner leg 48 of the suture 12 applies force against the outer side surface area 34 of the anchor 20 disposed between the outlet from the transverse passage 42 and the trailing end surface 38 of the anchor.

The force applied by the inner leg 48 of the suture against the outer side surface 34 of the anchor 20 causes the anchor to tip, as shown in FIG. 2, relative to the body tissue 14 and outer and inner inserter members 24 and 26. This tipping, that is, pivotal movement, is promoted by tensioning both the inner leg 48 and the outer leg 50 of the suture 12, as indicated by arrows 80 and 82 in FIG. 2. Thus, tensioning the inner leg 48 of the suture 12 presses the inner leg of the suture against the outer side surface area 34 disposed on the anchor 20 between the transverse passage 42 and the trailing end surface 48 (FIG. 2) to initiate tipping, that is, pivotal movement, of the anchor. At the same time, the tension in the leg 50 of the suture 12 applied force to the transverse passage 40 to continue the pivoting or tipping movement of the anchor 20.

As this tipping movement of the anchor 20 continues, the trailing end surface 38 on the anchor 20 slides across the leading end surface 54 on the tubular inner inserter member 26. As this occurs, an arcuate portion of the trailing end of the anchor 20 moves into and out of the passage 30 in the tubular inner inserter member 26, as shown schematically in FIG. 3. Thus, as the anchor 20 tips from the position shown in FIG. 2, through the position shown in FIG. 3 and toward the position shown in FIG. 4, the trailing end of the anchor slides along the circular rim on the leading end of the inner inserter member 26. As this occurs, a portion of the trailing end of the anchor 20 will rock into and out of the passage 30 in the inner inserter member 26.

The tension in the inner and outer legs 48 and 50 of the suture 12 causes the trailing end surface 38 of the anchor to slide along the leading end portion of the inner inserter member 26 from the position shown in FIG. 3 to the position shown in FIG. 4. As this occurs, the anchor 20 is effective to displace the relatively soft cancellous bone 72 disposed on opposite sides of the central axis of the recess 76 and inserter assembly 18. As the tipping movement or rotation of the anchor continues, the leading end surface 54 on the inner inserter member 26 moves into engagement with the cylindrical outer side surface 34 on the anchor 20 at a location between the outlet to the passage 42 and the trailing end surface 38 of the anchor 20 (FIG. 4).

Continued tensioning of the legs 48 and 50 of the suture 12 rotates the anchor to an orientation in which the longitudinal central axis of the anchor 20 is perpendicular to and extends through the longitudinal central axis of the inserter assembly 18 (FIG. 5). The tension in the inner and outer legs 48 and 50 of the suture 12 presses the cylindrical outer side surface 34 on the anchor 20 against the annular leading end surface 54 on the inner inserter member 26.

At this time, the anchor 20 has deflected the soft cancellous bone 72 and projects sidewardly of the recess 70 into the soft cancellous bone. This is because the anchor 20 has an axial extent which is greater than the diameter of the cylindrical recess 70. The suture 12 is then tensioned. Force is applied by the connector portion 58 of the suture 12 against the outer side surface 34 of the anchor 20 to press the anchor against the leading end surface 54 on the inner inserter member 26.

The inner inserter member 26 is then withdrawn from the recess 70. As this occurs, tension is maintained in the inner and outer legs 48 and 50 of the suture 12. This tension results in the anchor 20 being pulled axially upward (as viewed in FIG. 5) in the soft cancellous bone tissue 72 toward the hard outer layer 70 of cortical bone. As this occurs, the soft cancellous bone tissue 72 is deflected by portions of the outer side surface 34 of the anchor 20 located axially outward from the outlets of the transverse passages 40 and 42 through the anchor 20.

Figure 6:
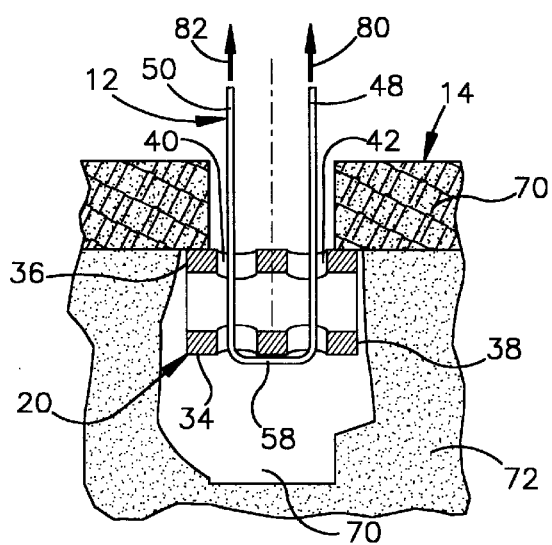
FIG. 6 is a simplified sectional view illustrating the manner in which the suture is tensioned to position the anchor relative to body tissue.

As the inserter assembly 18 is withdrawn from the recess 70, the anchor 20 moves to the position shown in FIG. 6. At this time, the cylindrical outer side surface 34 on the anchor 20 is pressed against the hard cortical outer layer 70 of bone or body tissue 14 by the tension in the legs 48 and 50 of the suture 12. Thus, tension force in the legs 48 and 50 of the suture 12 is applied against the outer side surface 34 of the anchor 20 at a location between the transverse passages 40 and 42 by the connector portion 58 of the suture 12. This force presses cylindrical surface areas disposed on the anchor 20 axially outward of the transverse passages 40 and 42 against the hard cortical outer layer 70 of bone.

At this time, a portion of the outer side surface 34 of the anchor 20 disposed between the transverse passage 40 and the end surface 36 of the anchor is pressed against the hard cortical outer layer 70 of bone (FIG. 6). In addition, a portion of the outer surface 34 disposed between the transverse passage 42 and the end surface 38 of the anchor 20 is pressed against the hard cortical outer layer 70 of bone. This results in the anchor 20 being firmly held in place in the body tissue 14 against relatively large pull-out forces in the suture 12.

Although the foregoing description has related to the positioning of the anchor 20 in hard body tissue 14 (bone), the anchor could be used in association with soft body tissue. The anchor may be positioned relative to the soft body tissue without forming a recess in body tissue.

Alternative Suture Arrangements

One specific manner of connecting the suture 12 with the anchor 20 is illustrated in FIGS. 1–6. However, it is contemplated that the suture 12 could be positioned in many different ways in the transverse passages 40 and 42 in the anchor 20. Some of these arrangements of the suture 12 relative to the anchor 20 are illustrated schematically in FIGS. 7 through 10. It should be understood that the anchor and inserter assembly of FIGS. 7–10 have the same general construction as the anchor 20 and inserter assembly 18 of FIGS. 1–6. However, the orientation of the anchor relative to the inserter assembly and/or the manner in which the suture is routed through the anchor and/or inserter assembly is modified in the arrangements shown in FIGS. 7–10.

In order to facilitate a comparison of the anchor and suture positions shown in FIGS. 7–10 with the anchor and suture positions shown in FIGS. 1 and 2, the same numerals will be utilized to designate the same portions of the anchor, suture and inserter assembly. However, the suffix letter "a" will be associated with the numerals of FIG. 7, the suffix letter "b" will be associated with the numerals of FIG. 8, the suffix letter "c" will be associated with the numerals of FIG. 9, and the suffix letter "d" will be associated with the numerals of FIG. 10 in order to avoid confusion.

In the embodiment of FIG. 7, the legs 48a and 50a of the suture 12a are routed or inserted through the transverse passages 40a and 42a in the anchor 20a in the same manner as is illustrated in FIG. 1. However, the position of the anchor in FIG. 7 is offset by 180° from the position shown in FIG. 1. Thus, the annular end surface 36a on the anchor 20a (FIG. 7) is disposed adjacent to the annular end surface 54a on the inner member 26a of the inserter assembly 18a. The annular end surface 38a on the anchor 20a is disposed adjacent to the lower (as viewed in FIG. 7) end of the cylindrical recess 70a. The recess 70a extends through the hard outer layer 70a of cortical bone into the soft inner layer 72a of cancellous bone.

The leg 48a of the suture 12a still extends through the transverse passage 42a. Similarly, the leg 50a of the suture 12a still extends through passage 40a and along the outside of the outer inserter member 24a. However, since the passage 42a is disposed further from the end surface 54a of the inner inserter member 26a with the arrangement shown in FIG. 7 than with the arrangement shown in FIG. 1, tensioning the legs 48a and 50a of the suture 126a applies force against the outer side surface 34a of the anchor 20a along a relatively long length of the outer side surface of the anchor and of the leg 48a of the suture. This promotes tipping, that is, pivotal movement, of the anchor 20a in the body tissue 14a.

In the embodiment illustrated in FIG. 8, anchor 20b is disposed in the same orientation relative to inserter assembly 18b as is the anchor 20 relative to the inserter assembly 18 of FIG. 1. However, in the embodiment of FIG. 8, legs 48b and 50b of suture 12b both extend through passage 30b in inner inserter member 26b. Therefore, both legs 48b and 50b of the suture 12b are enclosed by the outer member 24b and inner member 26b of the inserter assembly 18b.

When the suture legs 48b and 50b (FIG. 8) are tensioned to initiate tipping movement of the anchor 20b, both legs of the suture 12b apply force against the outer side surface 34b of the anchor 20b. Since both legs 48b and 50b of the suture 12b extend through the inner inserter member 26b, tension in the legs of the suture will tend to center the anchor 20b relative to the inner member 26b of the inserter assembly 18b when the anchor 20b is in the orientation shown in FIG. 5 for the anchor 20.

When the anchor 20b (FIG. 8) is in the orientation shown in FIG. 5 for the anchor 20, the longitudinal central axis of the anchor 20b (FIG. 8) will extend perpendicular to and intersect the central axis of the inserter assembly 18b. The suture leg 48b will apply force against the transverse passage 42b urging the anchor 20b axially toward the left (as viewed in FIG. 8). At the same time, the suture leg 50b will apply force against the transverse passage 40b urging the anchor 20b toward the right (as viewed in FIG. 8). The oppositely directed forces applied against the anchor 20b by the tension in the suture legs 48b and 50b results in the anchor 20b being positively centered relative to the inner inserter member 26b when the anchor 20b is in the orientation shown in FIG. 5 for the anchor 20. At this time, the central axis of the inserter assembly 18b will extend through the center of the anchor 20b at a location midway between the transverse passages 40b and 42b and midway between the end surfaces 36b and 38b of the anchor.

In the embodiment of the invention illustrated in FIG. 9, the outer inserter member 24c and the inner inserter member 26c are provided with arcuate notches or recesses to accommodate the legs 48c and 50c of the suture 12c. Thus, a notch 100 is provided in the end portion of the outer inserter member 24c to accommodate the leg 50c of the suture 12c. The notch 100 prevents the leg 50c of the suture 12c from being pinched between the outer inserter member 24c and the hard cortical outer layer 70c of bone.

A notch 102 is provided in the lower (as viewed in FIG. 9) end portion of the inner inserter member 26c to accommodate the leg 48c of the suture 12c. By providing the notches 100, the suture 12c is not pinched between the outer inserter member 24c and the hard cortical outer layer 70c of bone. The provision of the notch 102 in the inner inserter member 26c prevents the suture 12c from being pinched between the inner inserter member and the end surface 38c on the anchor 20c.

In the embodiment illustrated in FIG. 10, the leg 48d of the suture 12d extends between the inner inserter member 26d and the anchor 20d through a notch 102d in the inner member of the inserter assembly 18d. The leg 50d of the suture 12d extends through notch 102 and a notch 104 in the inner member 26d of the inserter assembly 18d. The leg 50d of the suture 12d also extends through a notch 100d in the outer member 24d of the inserter assembly 18d. The notches 100d, 102d and 104 all have an arcuate configuration.

In the arrangement illustrated in FIG. 10, the leg 50d of the suture 12d extends from the transverse passage 40d diametrically across the circular end surface 38d of the anchor 20d to the opposite side of the inserter assembly 18d. Thus, as viewed in FIG. 10, the outlets from the passages 40d and 42d face toward the left while the leg 50d is disposed on the right of the inserter assembly 18d. This results in the leg 50d of the suture 12d applying force against the cylindrical outer side 34d of the anchor 20d at a location between the transverse passage 42d and the end surface 38d of the anchor 20d to pull the upper (as viewed in FIG. 10) end portion of the anchor across to the opposite side of the inner inserter member 26d when the leg 50d of the suture 12d is tensioned. At the same time, tension in the leg 48d of the suture 12d promotes pivoting of the anchor 20d toward the orientation shown in FIG. 5 for the anchor 20.

In the illustrated embodiments of the invention, the anchor 20 is inserted into hard body tissue 14, that is, bone. However, the anchor 20 could be inserted into soft body tissue if desired. The anchor 20 may be utilized to apply force against the soft body tissue in much the same manner as disclosed in U.S. Pat. No. 5,464,426.

Conclusion

In view of the foregoing description, it is apparent that the present invention provides a new and improved method of anchoring a suture 20 in body tissue 14. The method includes inserting a suture 12 through a pair of spaced apart transverse passages 40 and 42 in an anchor. The suture 12 is moved into body tissue 14 with an end surface 38 on the anchor in engagement with a leading end 54 of an inserter member 26.

When the anchor 20 has been moved into the body tissue 14, the suture 12 is tensioned and the anchor is tipped under the influence of force applied to the anchor by the suture. Tipping of the anchor 20 results in movement of the anchor to a position in which the longitudinal central axis of the anchor extends transverse to a longitudinal central axis of the inserter member 26.

Having described the invention, the following is claimed:

1. A method of anchoring a suture, said method comprising the steps of: providing an inserter member having a longitudinal central axis and a leading end surface; providing an anchor having a longitudinal central axis and first and second passages which are spaced apart along the longitudinal central axis of the anchor and extend transversely to the longitudinal central axis of the anchor, the first passage being spaced from a first end surface on the anchor and the second passage being spaced from a second end surface on the anchor, the anchor having a first side surface area which extends from the first passage to the first end surface on the anchor and a second side surface area which extends from the second passage to the second end surface on the anchor; inserting the suture through the first and second passages in the anchor with a first portion of the suture extending from the first passage, a second portion of the suture extending from the second passage and a third portion of the suture extending between the first and second passages; moving the anchor along a path into body tissue with the first end surface on the anchor leading and the second end surface on the anchor engaging the leading end surface on the inserter member; said step of moving the anchor into body tissue being performed with the first passage in the anchor ahead of the second passage in the anchor and with the suture spaced from the first end surface on the anchor; said step of moving the anchor into body tissue being performed with the first portion of the suture extending from the first passage in the anchor through an opening in the body tissue to a location disposed to one side of the body tissue and with the second portion of the suture extending from the second passage in the anchor through the opening in the body tissue to the location disposed to one side of the body tissue; tensioning the suture to apply force to the anchor with the suture; tipping the anchor and moving the second end surface on the anchor at least part way across the leading end surface on the inserter member under the influence of force applied to the anchor by the suture to move the anchor to a position in which the longitudinal central axis of the anchor extends transversely to the longitudinal central axis of the inserter member; and, thereafter, pressing the first side surface area disposed on the anchor between the first end surface on the anchor and the first passage from which the first portion of the suture extends against body tissue offset to a first side of the opening in the body tissue and pressing a second side surface area disposed on the anchor between the second end surface on the anchor and the second passage from which second portion of the suture extends against body tissue offset to a second side of the opening in the body tissue under the influence of force applied against the anchor by the third portion of the suture which extends between the first and second passages.

2. A method as set forth in claim 1 wherein said steps of tensioning the suture and tipping the anchor include applying force against a surface area disposed on the anchor between the second passage and the second end surface on the anchor with a portion of the suture.

3. A method as set forth in claim 1 wherein said step of moving the anchor into body tissue is performed with the second portion of the suture extending from the second passage in the anchor into a passage in the inserter member, said steps of tensioning the suture and tipping the anchor include applying force against a surface area disposed on the anchor between the second passage and the second end surface on the anchor with the second portion of the suture.

4. A method as set forth in claim 1 wherein said step of moving the anchor into body tissue is performed with the first portion of the suture extending from the first passage in the anchor into a passage in the inserter member, said steps of tensioning the suture and tipping the anchor include applying force against a surface area disposed on the anchor between the first passage and the second end surface on the anchor with the first portion of the suture.

5. A method as set forth in claim 1 wherein said step of moving the anchor into body tissue is performed with the first and second portions of the suture extending from the first and second passages in the anchor into a passage in the inserter member, said steps of tensioning the suture and tipping the anchor include applying force against a surface area disposed on the anchor with the first and second portions of the suture.

6. A method as set forth in claim 1 wherein said steps of tipping the anchor and moving the second end surface on the anchor at least part way across the leading end surface on the inserter include moving a portion of the second end surface on the anchor into and out of a passage in the inserter member.

7. A method as set forth in claim 1 wherein said step of moving the anchor along a path into body tissue includes pressing the leading end surface on the inserter member against the second end surface on the anchor with a portion of a leading end of the inserter member extending across the second portion of the suture to transmit force from the inserter member to the anchor.

8. A method as set forth in claim 1 wherein said step of moving the anchor along a path into body tissue includes pressing the leading end surface on the inserter member against the second end surface on the anchor with a portion of a leading end of the inserter member extending across the first portion of the suture to transmit force from the inserter member to the anchor.

9. A method as set forth in claim 1 wherein said step of moving the anchor along a path into body tissue includes pressing the leading end surface on the inserter member against the second end surface on the anchor and against the first and second portions of the suture to transmit force from the inserter member to the anchor.

10. A method as set forth in claim 1 wherein said steps of pressing the first and second side surface areas disposed on the anchor against body tissue offset to first and second sides of the opening in the body tissue is performed with the suture spaced from the first and second end surfaces on the anchor.

11. A method of anchoring a suture, said method comprising the steps of: providing an inserter member having a longitudinal central axis and a passage which extends through the inserter member; providing an anchor having a longitudinal central axis and first and second passages which are spaced apart along the longitudinal central axis of the anchor and extend transversely to the longitudinal central axis of the anchor; inserting the suture through the first and second passages in the anchor with a first portion of the suture extending from the first passage, a second portion of the suture extending from the second passage and a third portion of the suture extending between the first and second passages; moving the anchor into body tissue with the longitudinal central axis of the anchor parallel to the longitudinal central axis of the inserter member; said step of moving the anchor into body tissue being performed with the first portion of the suture extending from the first passage in the anchor through the passage in the inserter member and with the second portion of the suture extending from the second passage in the anchor through the passage in the inserter member; tensioning the suture to apply force to the anchor with the suture; tipping the anchor under the influence of force applied to the anchor by the suture to move the anchor to a position in which the longitudinal central axis of the anchor extends transversely to the longitudinal central axis of the inserter member; and pressing the anchor against an end of the inserter member under the influence of tension in the first and second portions of the suture while the first and second portions of the suture extend through the passage in the inserter member.

12. A method as set forth in claim 11 wherein said steps of tensioning the suture and tipping the anchor include applying force against a surface area disposed on the anchor between the second passage and an end surface on the anchor with the first and second portions of the suture.

\* \* \* \* \*